(12) United States Patent
Wilmot et al.

(10) Patent No.: US 11,844,932 B2
(45) Date of Patent: Dec. 19, 2023

(54) SLIP-RESISTANT AUTOINJECTORS

(71) Applicant: Mylan Specialty L.P., Canonsburg, PA (US)

(72) Inventors: John Glyndwr Wilmot, Mount Airy, MD (US); Mark B. Bremley, Columbia, MD (US)

(73) Assignee: Mylan Specialty L.P.

( * ) Notice: Subject to any disclaimer, the term of this patent is extended or adjusted under 35 U.S.C. 154(b) by 130 days.

(21) Appl. No.: 16/913,042

(22) Filed: Jun. 26, 2020

(65) Prior Publication Data

US 2020/0324049 A1 Oct. 15, 2020

Related U.S. Application Data

(63) Continuation of application No. 16/125,926, filed on Sep. 10, 2018, now abandoned, which is a continuation of application No. 15/259,145, filed on Sep. 8, 2016, now abandoned, which is a continuation of application No. 13/976,494, filed as application No. PCT/IB2011/056031 on Dec. 30, 2011, now abandoned.

(60) Provisional application No. 61/428,297, filed on Dec. 30, 2010.

(51) Int. Cl.
*A61M 5/20* (2006.01)
*A61M 5/31* (2006.01)
*A61M 5/32* (2006.01)

(52) U.S. Cl.
CPC ........... *A61M 5/20* (2013.01); *A61M 5/3137* (2013.01); *A61M 5/3234* (2013.01); *A61M 2005/206* (2013.01); *A61M 2205/586* (2013.01)

(58) Field of Classification Search
CPC .................................................. A61M 5/3137
See application file for complete search history.

(56) References Cited

U.S. PATENT DOCUMENTS

| | | | | |
|---|---|---|---|---|
| 2,339,752 A | * | 1/1944 | Bilhuber | G10C 3/106 84/188 |
| 4,496,361 A | | 1/1985 | Kilkson | |
| 4,827,944 A | * | 5/1989 | Nugent | G01N 33/521 604/404 |
| 5,167,641 A | * | 12/1992 | Schmitz | A61M 5/3234 604/196 |
| 5,665,071 A | | 9/1997 | Wyrick | |
| 6,149,203 A | * | 11/2000 | Hanlon | G09F 3/0341 428/41.7 |

(Continued)

FOREIGN PATENT DOCUMENTS

| | | |
|---|---|---|
| WO | 200283212 A1 | 10/2002 |
| WO | WO-03086511 A1 * | 10/2003 .......... A61M 5/3129 |

*Primary Examiner* — Dung T Ulsh

(57) ABSTRACT

In an embodiment, the present invention provides an autoinjector that has one or more slip-resistant features. In certain embodiments, the exterior surface of the autoinjector housing forms at least one of indentures and protrusions that impart a slip-resistant texture to the housing of the autoinjector. In other embodiments, the one or more slip-resistant features are included on a label, which comprises a label substrate and is attached to the exterior surface of the housing of the autoinjector. The features are designed to improve the handling properties of the autoinjector and reduce the likelihood that the autoinjector will slip out of a user's or caregiver's hand during use.

13 Claims, 5 Drawing Sheets

(56) References Cited

U.S. PATENT DOCUMENTS

| | | | |
|---|---|---|---|
| 6,605,065 | B1 | 8/2003 | Tarentino |
| 8,535,274 | B2 | 9/2013 | Hjertman et al. |
| 11,049,420 | B2 * | 6/2021 | Utz .......................... G09F 3/10 |
| 2004/0116875 | A1 | 6/2004 | Fischer et al. |
| 2004/0267182 | A1 | 12/2004 | Davis |
| 2006/0011731 | A1 * | 1/2006 | Anders ................ G06K 19/077 |
| | | | 235/492 |
| 2006/0272208 | A1 | 12/2006 | Altman |
| 2008/0145620 | A1 | 6/2008 | Sahlberg |
| 2008/0188814 | A1 | 8/2008 | Lavi-Loebl et al. |
| 2010/0249697 | A1 | 9/2010 | Matusch |
| 2015/0079160 | A1 | 3/2015 | Doshi |
| 2017/0224934 | A1 * | 8/2017 | Shultz ................. A61M 5/3134 |

\* cited by examiner

SLIP-RESISTANT AUTOINJECTORS

BACKGROUND

Technical Field

The present invention relates to an autoinjector that has one or more slip-resistant features. The features are designed to improve the handling properties of the autoinjector and reduce the likelihood that the autoinjector will slip out of a user's or caregiver's hand during use.

Background Art

Autoinjectors have become quite popular and have experienced widespread use due to a variety of advantages autoinjectors have over typical manual syringe injectors. A number of autoinjectors are currently commercially available, including EpiPen® (King Pharmaceuticals Inc.), Anapen® (Lincoln Medical Ltd.), Rebiject® II (EMD Serono and Pfizer Inc.), and SureClick™ (Amgen). Generally speaking, an autoinjector is an automatic injection system that is designed to deliver a specific dosage of a medicament into an individual.

Among other things, autoinjectors generally comprise a housing having an exterior surface and an interior surface and a proximal and distal end, a medicament situated within the housing, a needle, and an activateable power assembly. After activation of the power assembly, the needle moves from a storage position in which the needle is situated within the housing to a medicament delivering position in which the needle extends out of the proximal end of the housing and delivers the medicament to a patient.

Often, a label containing, for example, instructions on how to use the autoinjector as well as a UPC code is attached to, and covers, a portion of the exterior surface of the autoinjector housing. Such labels, however, often have a slippery surface, which may decrease the handling properties of the autoinjector and increase the potential for the autoinjector to slip out of a user's or caregiver's hand.

BRIEF SUMMARY

In one aspect, the present invention provides an autoinjector that has one or more slip-resistant features. For example, in certain embodiments, the exterior surface of the autoinjector housing forms at least one of indentures and protrusions that impart a slip-resistant texture to the housing of the autoinjector.

In other embodiments, the one or more slip-resistant features are included on a label, which comprises a label substrate and is attached to the exterior surface of the housing of the autoinjector. For example, in one embodiment, the label comprises a label substrate and a varnish, wherein the varnish coats at least a portion of the label substrate. In yet another embodiment, the label comprises a label substrate having at least one of indentures and protrusions. In yet a further embodiment, the label comprises a label substrate and a film, wherein the film coats at least a portion of the label substrate and provides a matte finish to at least a portion of the label.

One or more of the slip-resistant features disclosed herein may be combined and the one or more slip-resistant features can be employed in any suitable autoinjector device. In addition to autoinjectors, the slip-resistant features can be employed in autoinjector training devices.

DETAILED DESCRIPTION

Figure 1:
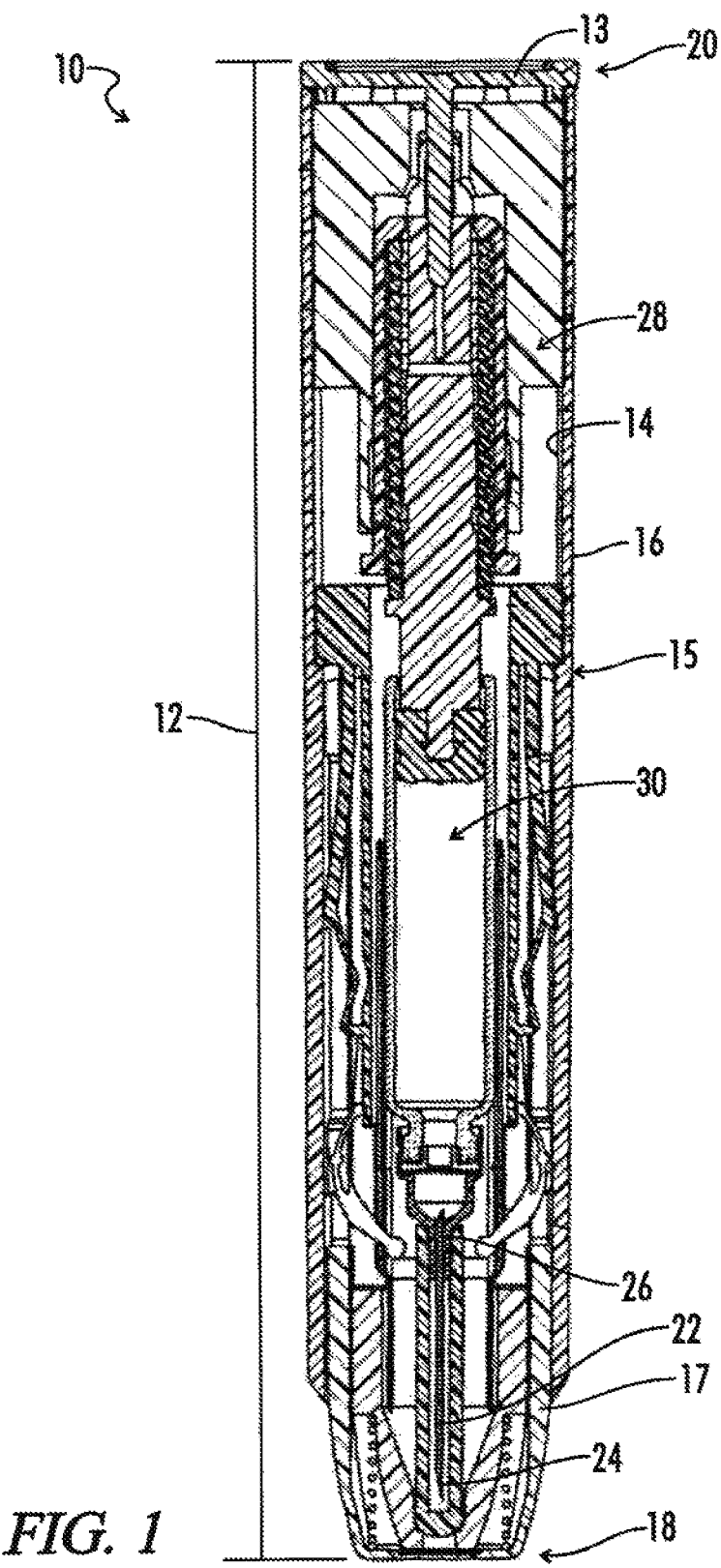
FIG. 1 illustrates a side cross-sectional view of an autoinjector.

Referring now to the drawings, FIG. 1 is provided to illustrate one embodiment of an autoinjector, designated by the numeral 10. In the drawings, not all reference numbers are included in each drawing for the sake of clarity. In addition, positional terms such as "upper," "lower," "side," "top," "bottom," etc. refer to the apparatus when in the orientation shown in the drawing. The skilled artisan will recognize that the apparatus can assume different orientations when in use.

Referring further to FIG. 1, and as known to those of ordinary skill, an autoinjector 10 typically includes a housing 12 having an interior surface 14 and an exterior surface 16 and a proximal end 18 and a distal end 20. The housing 12 forms the exterior surface of the autoinjector body and can include one or more structures. For example, in FIG. 1, the housing 12 comprises a safety pin 13, a cylindrical body 15 and a needle cover 17.

An autoinjector 10 also generally includes a needle 22, which has a proximal end 24 and a distal end 26 and is moveable from a needle storage position in which the needle 22 is situated within the housing 12 to a medicament delivering position in which the needle 22 extends out of the proximal end 18 of the housing 12. An autoinjector 10 also typically includes a power assembly 28 for moving the needle 22 from the needle storage position to the medicament delivering position and a liquid medicament 30 that is administered through the needle 22 as the needle 22 moves from the needle storage position to the needle fully extended position.

Figure 2:
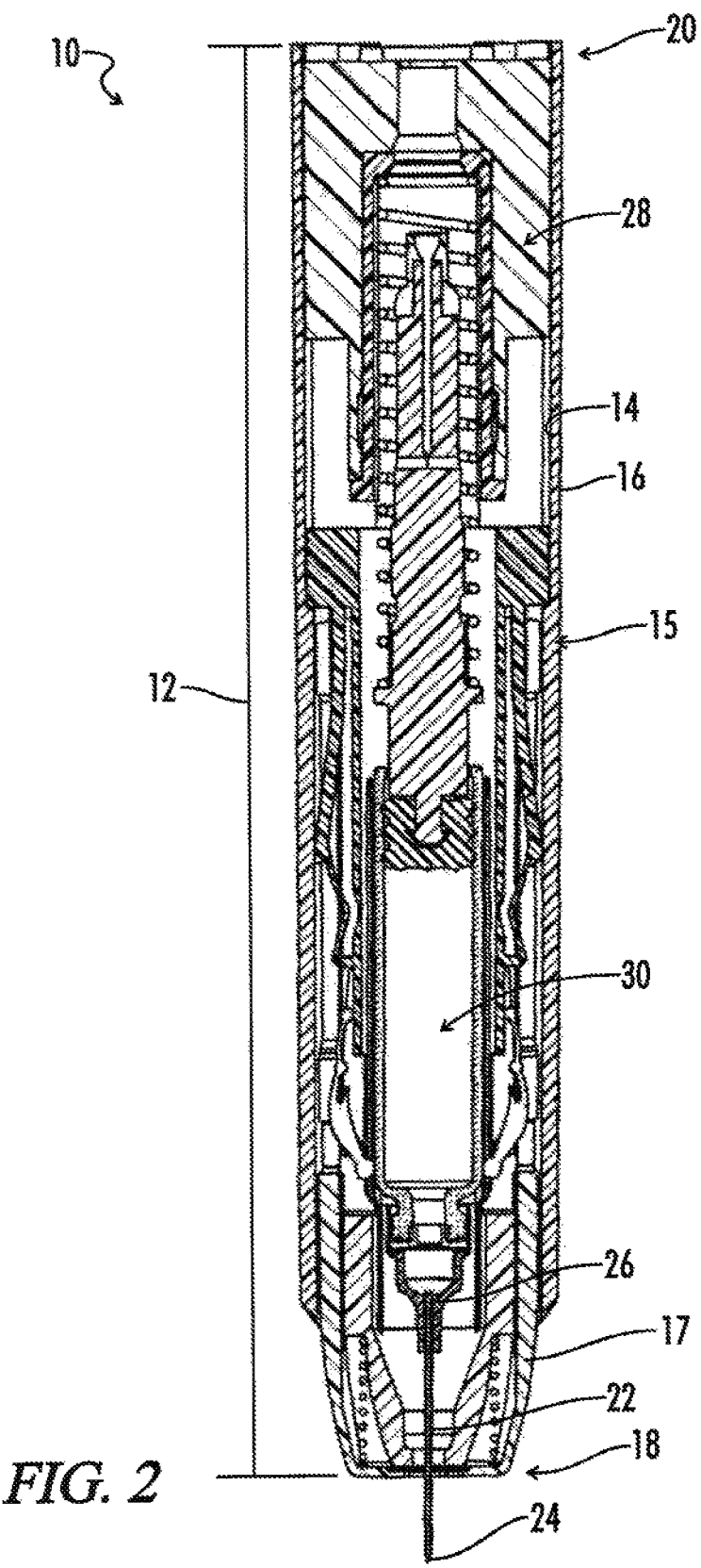
FIG. 2 provides a side cross-sectional view of an autoinjector in an activated state in which a needle is extending out of the proximal end of the housing of the autoinjector.

FIG. 2 is provided to illustrate an autoinjector 10 in an activated state in which the needle 22 has moved from the needle storage position.

As described in the Background Section above, the exterior surface of an autoinjector may be difficult to handle, especially in times of stress. Accordingly, the present invention provides an autoinjector that comprises one or more slip-resistant features.

For example, in one embodiment, a label comprising a varnish is provided to prepare an autoinjector that includes one or more slip-resistant features.

Figure 3:
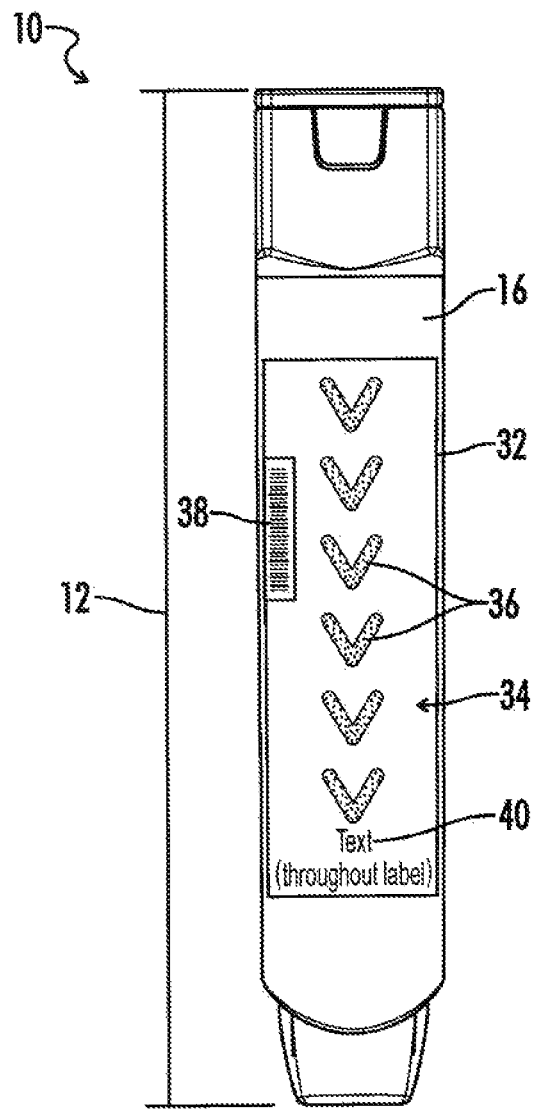
FIG. 3 is a side schematic view of an autoinjector having a label comprising a label substrate and a varnish.

As illustrated in FIG. 3, a label 32 including a label substrate 34 and a varnish 36 is attached to the exterior surface 16 of the housing 12 of an autoinjector 10. The varnish 36 coats at least a portion of the label substrate 34. As known to those of ordinary skill, a label substrate is the base upon which printing or other processes are performed to create a label. Optionally, the label 32 includes a UPC code 38 and one or more words 40 and/or pictures that provide, for example, instructions on how to use the autoinjector 10. Preferably, the label 32 covers at least about 30% of the exterior surface 16 of the housing 12.

Figure 7:
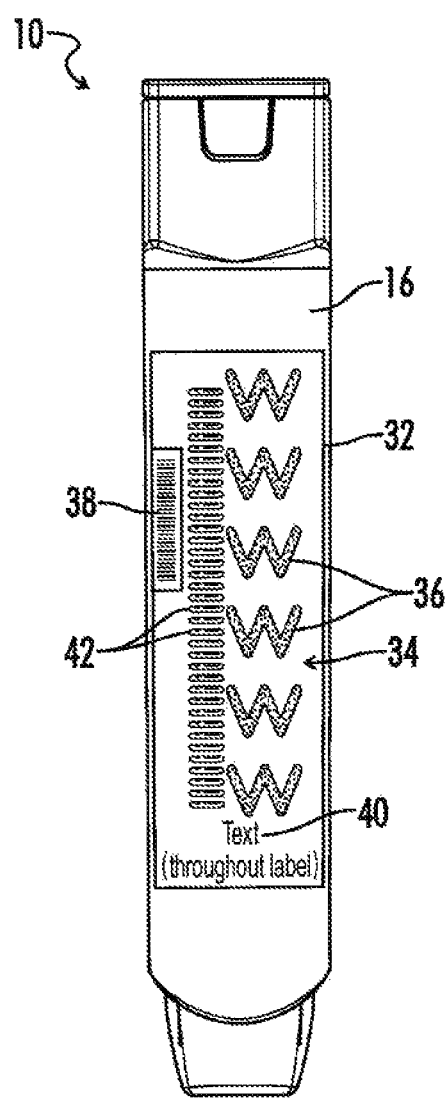
FIG. 7 is a side schematic view of an autoinjector having a label, which includes a label substrate and a varnish, wherein the label substrate includes indentures.

In certain embodiments, the varnish 36 forms a pattern on at least a portion of the label substrate 34. For example, as shown in FIG. 3, the varnish 36 can form a v-shaped pattern (also known as a chevron pattern) on the label substrate 34. Alternatively, as shown in FIG. 7, the varnish 36 can form a w-shaped pattern on the label substrate 34. It should be noted that the patterns of the varnish 36 have been enlarged in the drawings in FIGS. 3 and 7 so as to readily illustrate the patterns. Preferably, the size of the pattern the varnish 36 forms on the label substrate 34 is from about 0.25 millimeters by about 0.25 millimeters to about 2 millimeters by about 2 millimeters. Nonetheless, it will be appreciated that the range provided is exemplary and, for example, the varnish 36 can form larger patterns if desired. It is also preferred that the varnish 36 has one or more rubberized or textured, slip-resistant properties.

The varnish 36 can be any suitable material. For example, the varnish 36 can be a solvent- or epoxy-based varnish or the varnish can be a varnish that has been cured by ultraviolet light. Preferably, the varnish 36 has been cured by ultraviolet light. It is further preferred that the varnish 36 imparts a slip-resistant texture to at least a portion of the label 32. In certain embodiments, a gloss varnish is employed so as to facilitate reading of any words and/or pictures on the label while also providing a slip-resistant texture to at least a portion of the label.

Figure 4:
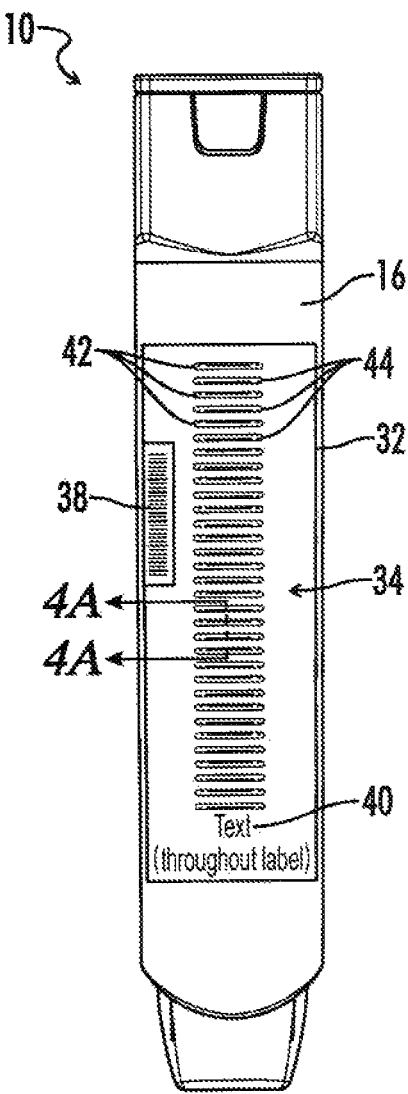
FIG. 4 is a side schematic view of an autoinjector having a label comprising a label substrate, wherein the label substrate includes indentures and protrusions.
Figure 4A:
FIG. 4A is a section view of the label substrate taken along line 4A-4A in FIG. 4.

In another embodiment, one or more indentures or protrusions are employed to create a slip-resistant label. More particularly, as illustrated in FIG. 4, a label 32 comprising a label substrate 34 having at least one of indentures 42 and protrusions 44 is attached to the exterior surface 16 of the housing 12 of the autoinjector 10. As shown in FIG. 4A, if present, the indentures 42 extend toward the exterior surface 16 of the housing 12 and the protrusions 44 extend away from the exterior surface 16 of the housing 12. In certain embodiments, the indentures 42 comprise microgrooves. In certain embodiments, the label substrate 34 is thermoformed so as to provide a slip-resistant label 32. In particular embodiments, the label substrate 34 is corrugated.

Figure 5:
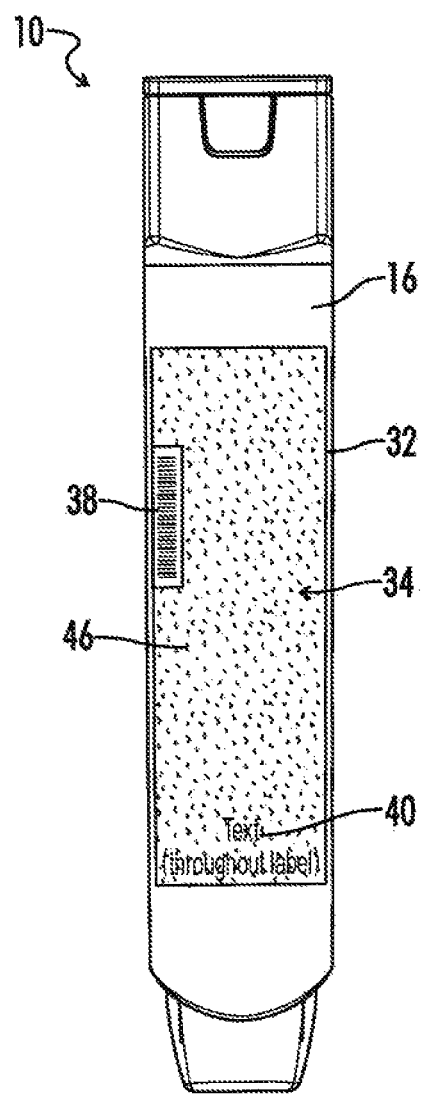
FIG. 5 is a side schematic view of an autoinjector having a label with a matte finish.

In another embodiment, as illustrated in FIG. 5, a label 32, which comprises a label substrate 34 and a film 46, is attached to the exterior surface 16 of the housing 12 of the autoinjector 10 to provide a slip-resistant autoinjector. The film 46 coats at least a portion of the label substrate 34 and provides a matte finish to at least a portion of the label 32.

Figure 6:
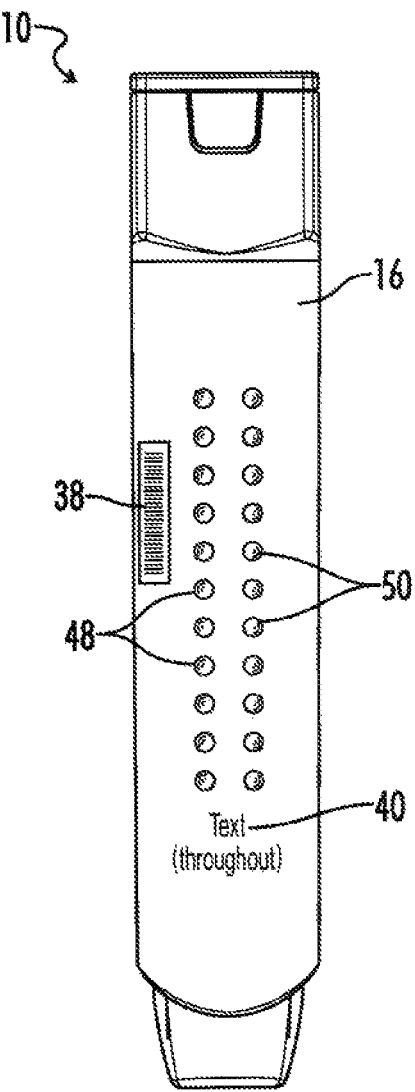
FIG. 6 is a side schematic view of an autoinjector, wherein the exterior surface of the autoinjector housing forms at least one of indentures and protrusions.

In yet another embodiment, instead of, or in addition to, including a slip-resistant label, the housing of the autoinjector can be molded with a slip-resistant surface or features and then the surface can be over printed with words and/or pictures using various printing processes, including, for example, ink jet printing, pad printing, laser printing, or in mold decorating. For example, as shown in FIG. 6, the exterior surface 16 of the housing 12 of the autoinjector 10 can form one or more indentations 48 or protrusions 50 to impart a slip-resistant texture. For example, in a particular embodiment, the exterior surface 16 of the housing 12 of the autoinjector 10 can include one or more indentations 48 that are sized and spaced so as to accommodate one or more fingers of a human user or caregiver. Additionally, the one or more protrusions 50 may form a flange for improving the handling properties of the autoinjector 10. If present, preferably, the flange is located at the proximal end 18 of the housing 12.

It will be appreciated that one or more of the slip-resistant features described above may be combined. For example, as illustrated in FIG. 7, a label 32 comprising a label substrate 34, which includes indentures 42, and a varnish 36 coating at least a portion of the label substrate 34 can be used to prepare a slip-resistant autoinjector 10.

Additionally, the autoinjector 10 can include both a slip-resistant label 32 as well as a slip-resistant housing 12. For example, the autoinjector 10 can include a slip-resistant label 32 comprising a label substrate 34 and a varnish 36 coating at least a portion of the label substrate 34, and the exterior surface 16 of the housing 12 of the autoinjector 10 can form one or more indentations 48 or protrusions 50 to impart a slip-resistant texture. In such an embodiment where the autoinjector 10 includes both a slip-resistant label 32 as well as a slip-resistant housing 12, preferably, the label 32 contains words and/or pictures, such as user instructions, and the exterior surface 16 of the housing 12 is over printed with words and/or pictures. It is further preferred in this embodiment that the label 32 covers less than about 30% of the exterior surface 16 of the housing 12.

In addition to the one or more slip-resistant features described above, the autoinjector can employ any features or structures known in the art or later developed, including without limitation those described in FIGS. 1 and 2 as well as those described in U.S. Pat. Nos. 7,449,012 and 7,811,254, the contents of which are incorporated herein in their entirety. Preferably, the autoinjector includes a needle and a power assembly as described above.

The slip-resistant features described above may also be employed in an autoinjector training device. Typically, autoinjector training devices resemble autoinjectors but do not include needles or medicaments. Autoinjector training devices are described in, for example, U.S. Pat. Nos. 4,640,686 and 5,567,160 and U.S. Patent Publication No. 2007/0111175, the contents of each of which are incorporated by reference in their entirety.

The one or more slip-resistant features preferably improve the handling properties of the autoinjector. For example, the slip-resistant features may be especially beneficial if the user's or caregiver's hands are wet, sweaty and/or covered with a lotion such as sunscreen, hand lotion, rubbing alcohol, and/or isopropyl alcohol.

Having now described the invention in accordance with the requirements of the patent statutes, those skilled in the art will understand how to employ the features of the invention and make changes and modifications to the disclosed embodiments to meet their specific requirements or conditions.

For example, the skilled artisan will appreciate that preferably any slip-resistant features included on an autoinjector or autoinjector training device do not affect the ease at which the autoinjector or autoinjector training device is manufactured and packaged. For example, the labeling and packaging of autoinjectors often requires that the labels be applied with wipers that can slide over the surface of the labels without resulting in wrinkles, bubbles or creases. Additionally, it is often desirable that labels be laid in flat wrap around the autoinjector housing to allow good adhesion and presentation. Thus, preferably, any slip-resistant features on the label do not interfere with the ease at which wipers can slide over the surface of the label. In addition, in certain embodiments, when wrapping the label around the autoinjector housing, the ends of the label may overlap with one another so that a portion of the label is adhered to another portion of the label. Thus, in such cases, preferably, the slip-resistant features do not interfere with the ability of a portion of the label to adhere to another portion of the label. Further, autoinjectors are frequently packaged into protective carriers, where they are carried prior to use. Thus, preferably the slip-resistant features do not increase the coefficient of friction of the label and/or the exterior surface of the autoinjector to such an extent so as to interfere with the packaging of the autoinjector in the protective carrier or the removal of the autoinjector from the protective carrier prior to use.

Additionally, coating a label substrate may decrease the readability of any printed material included in the label, including, without limitation, a UPC code or instructions. Thus, if the slip-resistant feature decreases the readability of any printed material to the extent that the material cannot be easily read by a user or computer, preferably, the feature is not included in the portion of the label that needs to be read by a user or computer. Furthermore, in certain embodiments, words may be imprinted on the label after a slip-resistant coating has been applied to the label substrate. Thus, preferably, words are not imprinted on the coating. Additionally, in certain embodiments, one or more slip-resistant features may be masked so that the features do not contact any features contained in the autoinjector protective carrier, including, without limitation, automation fixture surfaces and ribs in an autoinjector protective carrier.

EXAMPLES

The following example is provided to illustrate some embodiments of the present disclosure but should not be interpreted as any limitation thereon.

Example 1

This example exemplifies the applying of varnish to a label substrate.

Three different varnishes were obtained: EOP-18, 135 LP, and Varnish 329. Varnish EOP-18 has a viscosity of about 200 cps, Varnish 329 has a viscosity of about 1,500 cps and is thicker than EOP-18, and Varnish 135 LP has a viscosity of about 120 cps and is tackier than EOP-18 so as to give a "rubbery" or textured feel.

Each varnish was then applied to label substrates using seven different plates. One plate was smooth and others had a "v" (chevron) pattern or a bumped pattern. With each pattern, the texture was increased by 50% or decreased by 50% so that each varnish was applied in a smooth pattern, a standard bumped pattern, a standard "v" pattern, a 50% reduced bump pattern, a 50% reduced "v" pattern, a 150% bump pattern, and a 150% "v" shaped pattern.

The invention claimed is:

1. An autoinjector comprising:
a housing having an interior surface and an exterior surface and a proximal end and a distal end, and a medicament situated within the housing, wherein a slip-resistant label is attached to the exterior surface of the housing, wherein said slip-resistant label comprises a label substrate containing printing thereon, and wherein said slip-resistant label further comprises one of a coating selected from either a) a varnish coating at least a portion of the label substrate, wherein the varnish forms a pattern on at least a portion of the label substrate or has one or more rubberized or textured properties, or b) a film coating and providing a matte finish imparting a slip-resistant texture to at least a portion of the label substrate.

2. The autoinjector according to claim 1, wherein the slip-resistant label comprises the varnish coating at least a portion of the label substrate and the varnish forms a pattern on at least a portion of the label substrate.

3. The autoinjector according to claim 2, wherein the varnish has been cured by ultraviolet light.

4. The autoinjector according to claim 2, wherein the varnish is a solvent-based varnish or an epoxy-based varnish.

5. The autoinjector according to claim 2, wherein the varnish comprises a gloss varnish.

6. The autoinjector according to claim 2, wherein the varnish has one or more rubberized or textured properties.

7. The autoinjector according to claim 1, wherein the slip-resistant label covers at least about 30% of the exterior surface of the housing.

8. The autoinj ector according to claim 1, wherein the slip-resistant label comprises the film coating and providing a matte finish imparting a slip-resistant texture to at least a portion of the label substrate.

9. The autoinjector according to claim 1, wherein the slip-resistant label comprises the varnish coating at least a portion of the label substrate and wherein the varnish has one or more rubberized or textured properties.

10. The autoinjector according to claim 9, wherein the varnish has been cured by ultraviolet light.

11. The autoinjector according to claim 9, wherein the varnish is a solvent-based varnish or an epoxy-based varnish.

12. The autoinjector according to claim 9, wherein the varnish comprises a gloss varnish.

13. The autoinjector according to claim 1, wherein the label substrate has a slippery surface.

* * * * *